United States Patent [19]
Cheung

[11] Patent Number: 5,584,292
[45] Date of Patent: Dec. 17, 1996

[54] DIGITAL X-RAY CAMERA FOR PRECISION MAMMOGRAPHIC NEEDLE BIOPSY SYSTEM

[75] Inventor: Lim H. Cheung, Setauket, N.Y.

[73] Assignee: Grumman Aerospace Corporation, Los Angeles, Calif.

[21] Appl. No.: 331,895

[22] Filed: Oct. 31, 1994

[51] Int. Cl.⁶ .................................................. A61B 6/00
[52] U.S. Cl. ...................... 128/653.1; 378/37; 378/98.3
[58] Field of Search .......................... 128/653.1; 606/130; 250/370.09, 370.25; 378/37, 98.3

[56] References Cited

U.S. PATENT DOCUMENTS

| | | | |
|---|---|---|---|
| 4,020,347 | 4/1977 | Geluk | 250/361 R |
| 4,571,495 | 2/1986 | Distler et al. | 250/394 |
| 4,686,631 | 8/1987 | Ruud | 378/72 |
| 4,733,082 | 3/1988 | Moore et al. | 250/363 S |
| 4,821,727 | 4/1989 | Levene et al. | 128/653 |
| 4,860,205 | 8/1989 | Jatteau | 364/413.24 |
| 4,933,961 | 6/1990 | Rushbrooke et al. | 378/57 |
| 5,099,128 | 3/1992 | Stettner | 250/370.11 |
| 5,132,539 | 7/1992 | Kwasnick et al. | 250/361 |
| 5,142,557 | 8/1992 | Toker et al. | 378/37 |
| 5,150,394 | 9/1992 | Karellas | 378/62 |
| 5,189,686 | 2/1993 | Hixson, Sr. | 378/37 |
| 5,216,250 | 6/1993 | Pellegrino et al. | 250/370.09 |
| 5,229,613 | 7/1993 | Pandelisev et al. | 250/368 |
| 5,289,520 | 2/1994 | Pellegrino et al. | 378/37 |
| 5,404,387 | 4/1995 | Hammond et al. | 378/98.3 |
| 5,436,492 | 7/1995 | Yamanaka | 257/433 |

Primary Examiner—Ruth S. Smith
Attorney, Agent, or Firm—Terry J. Anderson; Karl J. Hoch, Jr.

[57] ABSTRACT

An imaging system for a precision mammographic needle biopsy system includes an x-ray camera whose housing includes a compression panel for the breast, a portion of the compression panel being transparent to X-rays that have passed through the breast so that the surface on which the breast is positioned forms the outside surface of the camera head. Adjacent the interior of the transparent surface, are a scintillator and optics for guiding an image formed when X-rays impinge upon the scintillation material to a CCD board within a hermetically sealed inner camera housing. The optics are in the form of a fiber optic coupler made up of a bundle of coherent optical fibers having scintillation material coated at ends thereof to provide appropriate magnification of the image, thereby eliminating the need for lenses or mirrors, image intensifiers, and the like, and providing improved resolution because of the direct coupling of the scintillation material at the ends of the fibers and the CCD array. The x-ray camera contains within its housing all necessary analog and digital circuitry, including clock signal generating circuitry, power and control circuitry, an analog-to-digital converter, and a digital bus interface, for processing and converting a captured image into a digital image suitable for transmission over a standard digital bus for further processing, the camera thus being compatible, without modification, with a wide variety of controllers and imaging processing equipment.

8 Claims, 6 Drawing Sheets

DIGITAL X-RAY CAMERA FOR PRECISION MAMMOGRAPHIC NEEDLE BIOPSY SYSTEM

BACKGROUND OF THE INVENTION

1. Field of the Invention

This invention relates to the field of radiography, and more particularly to apparatus for providing real-time radiographic monitoring of breast tissue during a stereotactic needle biopsy procedure.

2. Description of Related Art

X-ray mammography is a diagnostic procedure in which the breast of a patient is X-rayed and the resulting X-ray film is inspected to determine whether there are any microcalcifications or other growths or lesions in the breast tissue. If a lesion or growth is visible in the X-ray film, then it is often necessary to perform a biopsy procedure to determine if the lesion or growth is benign or if it requires immediate treatment. Although the X-ray film can be used to give a rough estimate of the position of the lesion, breast tissue is highly malleable and thus new images of the breast must be taken immediately before the biopsy procedure is performed, and after the breast has been compressed and clamped. In order to precisely locate the biopsy needle relative to the lesion, conventional equipment requires that multiple images be taken, which in turn necessitates repositioning and reclamping of the breast. Such procedures are time-consuming and uncomfortable for the patient.

Recently, systems have been developed which allow the breast to be clamped once, and the X-ray source moved to different positions and monitored on a video screen during the biopsy procedure in order to provide real time guidance of the biopsy needle without the need to reposition the breast each time a new image is taken. The present invention is designed to be used with systems of the general type disclosed in U.S. Pat. No. 4,821,727, and in particular with apparatus designed by Bennett Corporation and illustrated in FIG. 1 (which also shows a portion of the preferred invention).

In the Bennett system, and others of its type (including the one disclosed in U.S. Pat. No. 4,821,727), the patient to be examined is seated in a chair 10 which is adjustable so that the patient can be comfortably positioned with the breast to be examined being located on a table 24. An X-ray source 16 is mounted on a pivotal arm 18 so that the target area can be exposed to X-rays at different angles in order to form a stereoscopic image of the breast without having to unclamp and reposition the breast each time a new image is taken. However, in the Bennett system, instead of using two relatively movable plates to compress the breast, as disclosed in U.S. Pat. No. 4,821,727, a single movable plate 22 serves to compress the breast against a table top in order to keep it stationary and provide for a uniform X-ray exposure.

In the Bennett system, as in other similar systems, images captured by the X-ray camera device, to be described in detail below, are displayed on a monitor 28, and used by the physician to guide a biopsy needle 20 to a targeted tissue within the breast by means of an electronic controlled biopsy needle actuator and appropriate cursor controls for enabling azimuth, elevation, and depth of insertion adjustments to be made. Conventionally, an image of the needle is included in the image of the breast, and a variety of means are known for providing reference points in the display to assist in guiding of the biopsy needle to its target.

The present invention is an imaging system suitable for use with the Bennett apparatus illustrated in FIG. 1. However, it will be appreciated by those skilled in the art that the principles of the invention may be used with apparatus other than the Bennett apparatus specifically disclosed herein. These principles involve improvements in the x-ray camera used to capture the image and in the image processing circuitry which offer a number of advantages over imaging systems used in prior apparatus, including the imaging system disclosed in U.S. Pat. No. 4,821,727, cited above. In the system disclosed in U.S. Pat. No. 4,821,727, for example, the X-rays are first caused to strike a fluorescent screen, with the resulting visible light image being captured by a lens and video camera system. In order to provide a usable display, this prior imaging arrangement requires an "image intensifier" coupled to the fluorescent screen output via a mirror or prism and/or fiber optics (see col. 5, lines 50–65 of U.S. Pat. No. 4,821,727). Such an imaging system is both structurally complicated and lacks the error correction capabilities and other processing advantages of a digital system.

In U.S. Pat. No. 5,289,520, an X-ray mammography system is disclosed which utilizes a more sophisticated digital imaging system but less than optimal optics. In this type of system, the X-rays are captured by a phosphorescent plate, which in turn emits photons at visible light frequencies. The photons emitted by the phosphorescent plate are focused by a lens system onto a CCD array, and the output of the CCDs are applied through a preamplifier, transmitted over an analog bus, and subsequently digitized for further processing. While use of digital image enhancement software provides magnification, contrast enhancement, window level manipulation and high resolution images, with low exposure levels, short exposure times, and greatly reduced imaging time, and thus represents an improvement over the system disclosed in U.S. Pat. No. 4,821,727, digital systems of the type disclosed in U.S. Pat. No. 5,289,520 nevertheless have the disadvantage of being relatively complex, with little attention given to patient comfort (in the system disclosed in U.S. Pat. No. 5,289,520, for example, the patient must assume a relatively uncomfortable prone position for the duration of the imaging procedure, as opposed to the seated position shown in FIG. 1.

SUMMARY OF THE INVENTION

It is accordingly an objective of the invention to provide an imaging system for a precision mammographic needle biopsy system having optimized imaging hardware integrated into an apparatus which is ideal both from the standpoints of cost, reliability, and patient comfort.

This objective of the invention is accomplished by providing an improved x-ray camera which is particularly suitable for, although not necessarily limited to, apparatus of the type in which the patient sits in a chair so as to have one breast between a compression panel and a surface, and an X-ray source is mounted on a pivotal arm so as to allow angled direction of the radiation.

In one preferred embodiment of the invention, the imaging system includes an x-ray camera whose housing includes a compression panel for the breast, a portion of the compression panel being transparent to X-rays that have passed through the breast so that the surface on which the breast is positioned forms the outside surface of the camera head. In the x-ray camera of this embodiment, adjacent the interior of the transparent surface, are a scintillator and optics for guiding an image formed when X-rays impinge upon the scintillation material to a CCD board within the sealed camera housing. Advantageously, the optics are in the form of a planar fiber optic coupler made up of a bundle of coherent optical fibers providing appropriate magnification of the image, the scintillation material being in the form of a phosphor coating on the tips of the fibers adjacent the transparent surface, thereby eliminating the need for lenses or mirrors, image intensifiers, and the like, and providing improved resolution because of the direct coupling of the scintillation material at the ends of the fibers and the CCD array.

Additional advantages are obtained for the x-ray camera of the preferred embodiment by including analog and digital circuitry, including all necessary clock signal generating, power and control, external interface (including a microprocessor for interpreting commands from an external controller), and field programmable gate array (FPGA) circuitry, for processing the image captured by the CCD array and converting the image into a digital image suitable for transmission over a standard digital bus for further processing, the camera thus being compatible, without modification, with a wide variety of controllers and imaging processing equipment (particularly when FPGA logic circuitry is used for such purposes as generation of the clocking signals). For example, the camera may include a precision regulator for an analog offset and gain amplifier, correlated double sampling circuitry fed by the offset and gain amplifier, and a sample and hold circuit connected to an output of the correlated double sampling circuitry, the output of the sample and hold circuit being processed in this example by a 14-bit 1 MHz analog to digital converter and made available to a set of differential TTL line drivers to generate RS-422 compatible connections to a remote electronics box in which digital image processing takes place.

Those skilled in the art should appreciate, however, that the invention lies in the architecture of the system more than in any details of the circuitry used therein, and that once the architecture of the system is understood, details of the circuitry can readily be implemented, as a matter of routine circuit design, by those skilled in the art. In fact, the principal components of the system, such as the CCD array, are available in the form of commercially available integrated circuit packages which can easily be adapted for purposes of implementing the preferred circuitry.

In an especially advantageous embodiment of the invention, the camera CCD board is contained in a hermetically inner housing, which protects the patient from being exposed to either heat from the camera or the effects of cooling the camera. Heat exchange from inside the camera housing is preferably carried out by cooling fins provided in thermal contact with the camera CCD board, the interior of the sealed inner housing being cooled by a thermal electric heat pump to a temperature which enables efficient operation of the CCD arrays In conventional arrangements, rubber seals are used which will eventually allow moisture infiltration. By using hermetic sealing, the need for periodically purging the system of moisture is greatly reduced or eliminated.

The resulting design provides a camera head which is as small as possible for operational convenience while at the same time preserving the low noise and high dynamic range characteristics of the CCD at a competitive price. The system provides maximum flexibility in future networking capability and expansion. Its unique design allows the CCD gain and offset non-uniformities to be processed in real-time during the readout phase, with provisions for a memory-mapped storage buffer to facilitate data display on the computer system, allowing a fast and efficient image transfer and allowing an image to be viewed as soon as the CCD is read out. The system also provides digital drive circuitry based on EEPROM and FPGA technology which provides a fully software programmable digital clock and control lines for servicing the CCD sensor, as well as interfacing with the host computer. As a result, the circuitry can be adapted for different CCD sensor designs and dimensions and, as a new generation of CCDs become available, the same circuitry can be used with little or no modification.

The analog circuitry is also designed for maximum flexibility to accommodate future product upgrades, the use of double correlated sampling circuitry based on a dual-slope integrator providing a significant reduction in 1/f and reset noise. A low noise wide-bandwidth front and amplifier section provides sufficient noise margin to meet specified noise performance at a readout rate exceeding 200 kHz, providing the possibility for either a higher readout rate consistent with the shot noise limited performance, or when operated at −40° C., a higher dynamic range of up to 16-bits. The benefits of these upgrades translate into shorter waiting time for the patients when multiple X-rays are made, or better X-ray feature detection and recognition capabilities. The tight coupling and optimal partitioning of the camera electronics in the computer enhance data throughput which translates into better product acceptance.

DETAILED DESCRIPTION OF THE PREFERRED EMBODIMENTS

Figure 1:
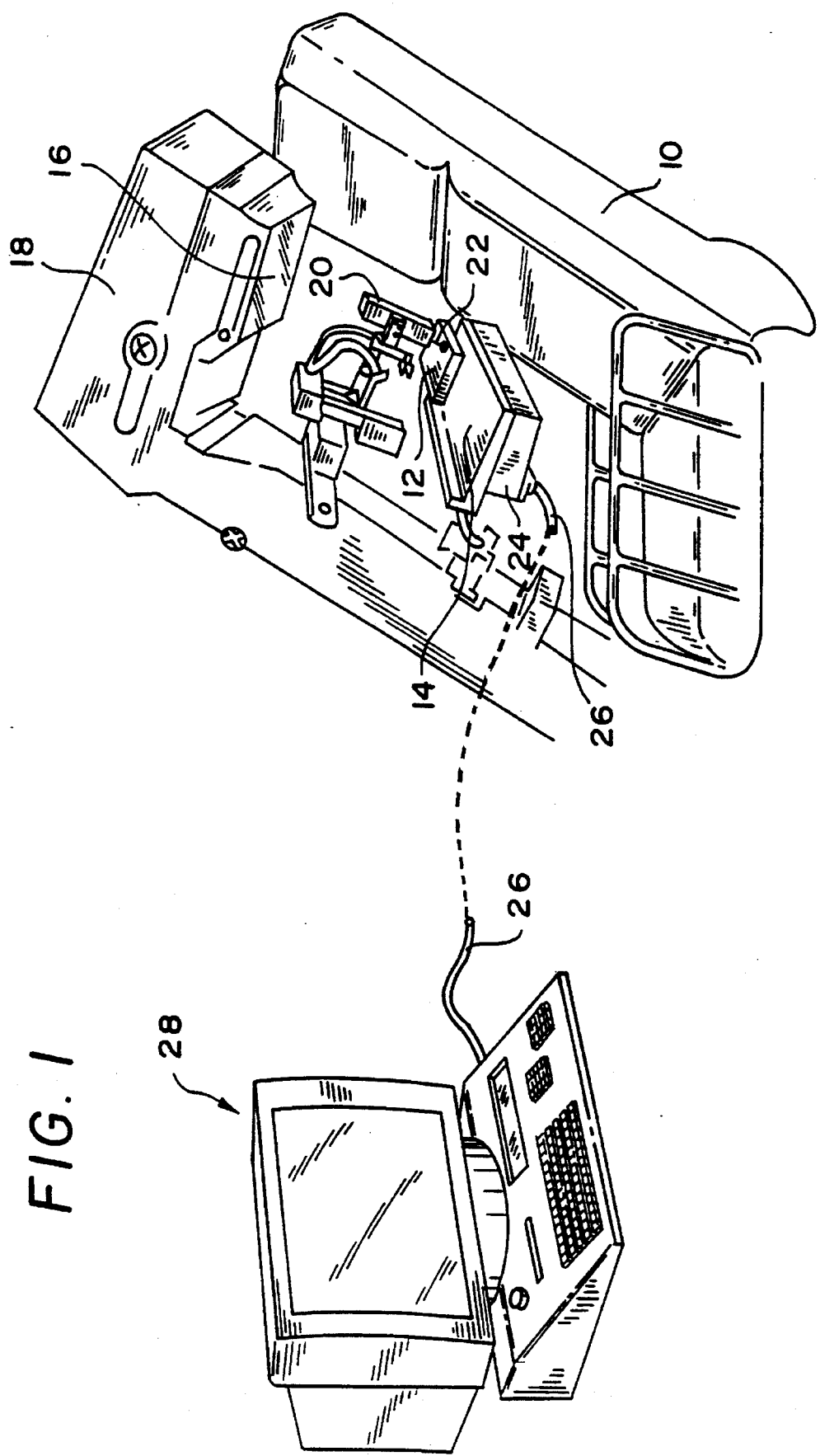
FIG. 1 is a perspective view of a mammographic needle biopsy apparatus which includes imaging components arranged in accordance with the principles of a preferred embodiment of the invention.

FIG. 1 is a perspective view of an operator and patient interface for a preferred x-ray camera and imaging system which makes up the preferred embodiment of the invention. The patient is seated in a chair 10 which is adjustable so that the patient can be comfortably positioned, with the breast to be examined located on a table 24. An X-ray source 16 is mounted on a pivotal arm 18 so that the target area can be exposed to X-rays at different angles in order to form a stereoscopic image of the breast. A plate 12 serves to compress the breast against the table top in order to keep it stationary and provide for a uniform X-ray exposure. Images captured by the X-ray camera device, which is housed within table 24, as will be described in detail below, are displayed on a monitor which is part of a personal computer or workstation 28, and used by the physician to guide a biopsy needle 14 to the targeted tissue within the breast by means of an electronically controlled biopsy needle actuator 20 and appropriate cursor controls.

The present invention concerns only the imaging portion of the apparatus, and not the actuator control, except to the extent that the output of the preferred imaging system may be used to provide actuator control (for example, image recognition techniques may be used to provide at least a degree of automatic control of the actuator).

Figure 2:
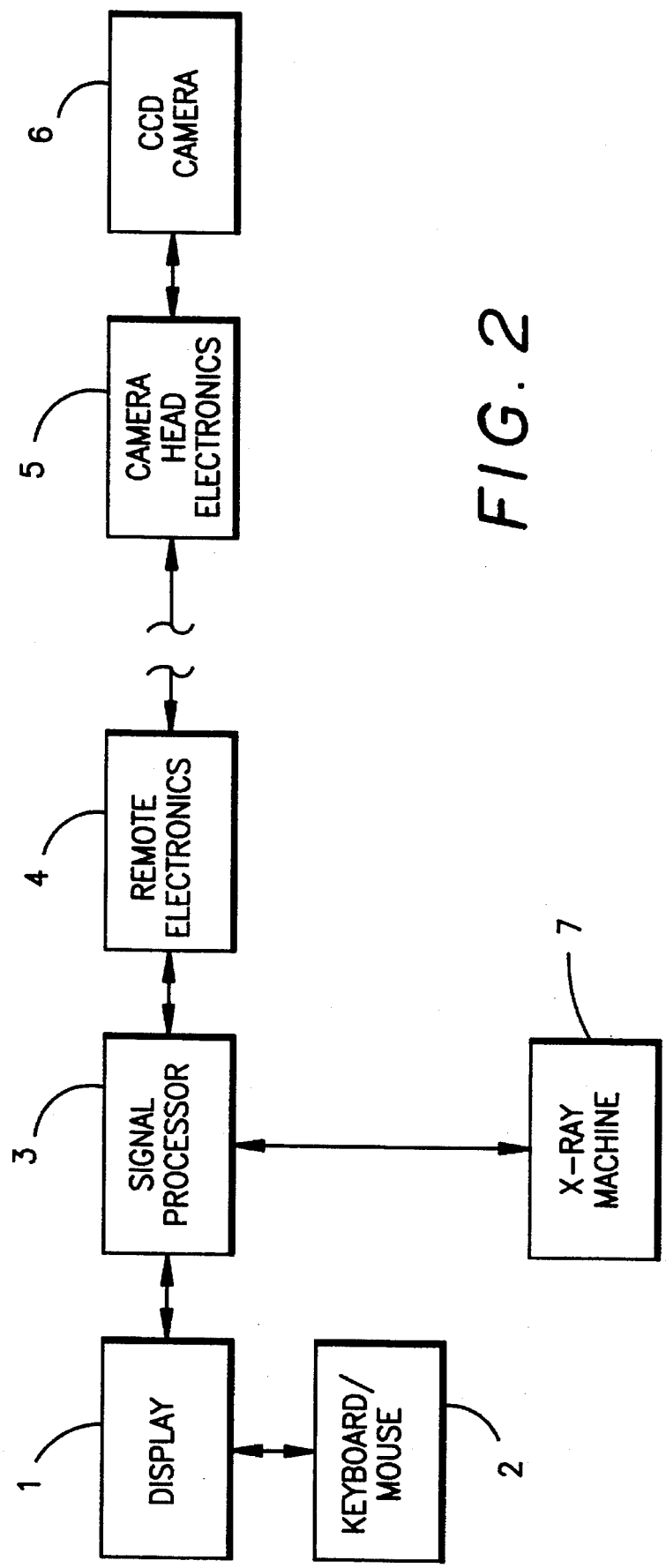
FIG. 2 is a functional block diagram of a preferred imaging system for the apparatus illustrated in FIG. 1.

An overview of the preferred imaging system is shown in FIG. 2. Details of the circuitry shown in FIG. 2 are illustrated in the remaining FIGS. 3–6, although those skilled in the art should appreciate that the details illustrated in the remaining Figures are merely exemplary in nature, having been provided for the purpose of disclosing the best mode known to the inventor and to enable those skilled in the art to make and use the invention, and therefore should not be viewed as limiting in any way except insofar as those details might be positively recited in any of the appended claims.

The principal components of the preferred imaging system include a display 1 situated such that the physician performing the biopsy can view it during a procedure, while manipulating a keyboard or mouse control 2. A signal processor 3 is provided to supply the processed image to a display, and to generate and transmit the necessary control signals for the X-ray machine 7 and the imaging system, which consists of the CCD camera 6, camera head electronics 5, and remote electronics 4, elements 4–6 being described in detail below, while elements 1–3 and 7 may be conventional.

Figure 3:
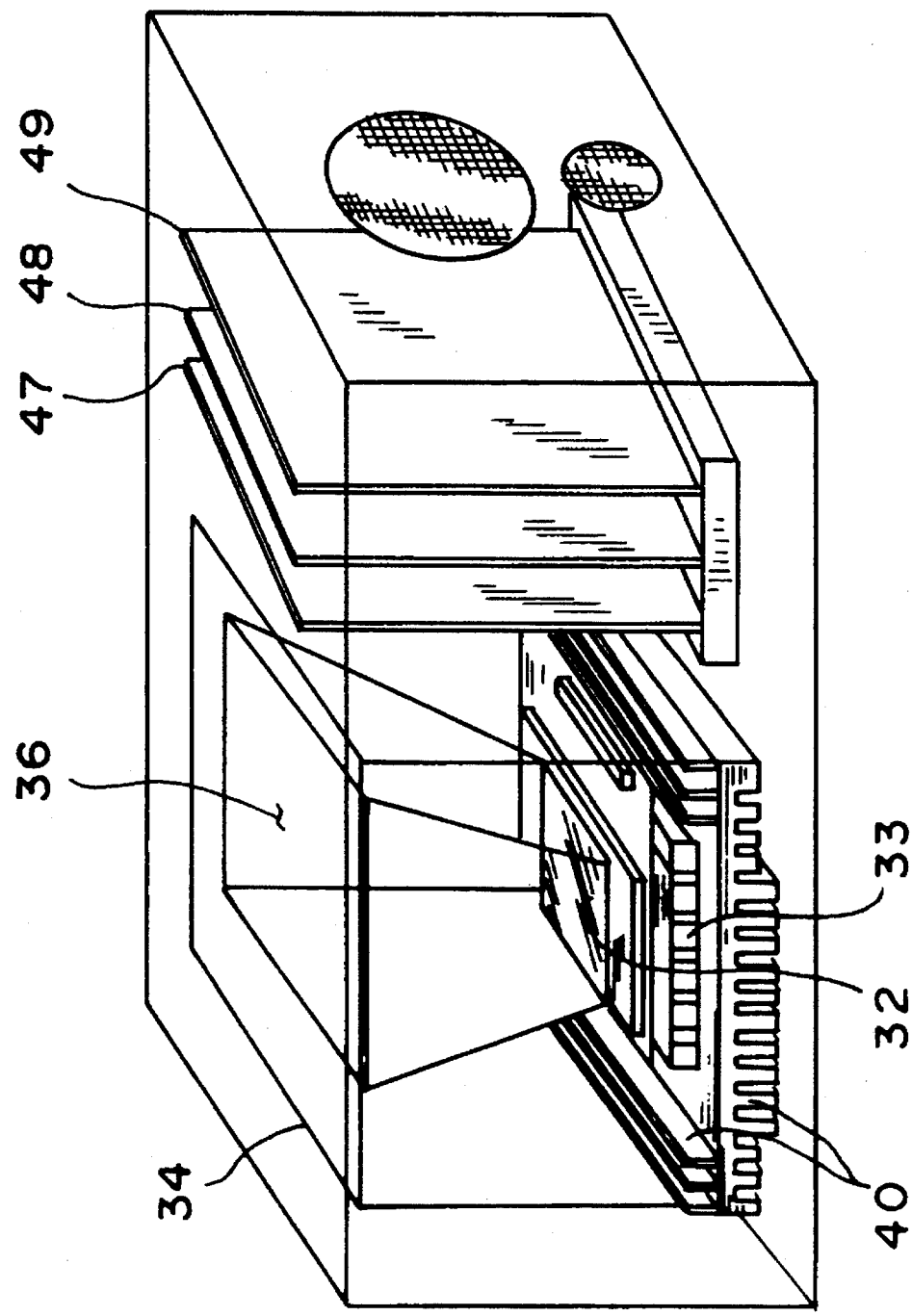
FIG. 3 is a perspective view of a camera head for the preferred imaging system shown in FIG. 2.

A detailed view of the camera head for the preferred X-ray imaging system is shown in FIG. 3. The camera head housed in table 24 is advantageously extremely compact in size, measuring as little as 3.5"×3.5"×5" yet contains not only the camera itself, but also processing electronics including analog-to-digital conversion, and cooling apparatus arranged to protect the camera electronics while reducing patient discomfort which caused by overheating of the camera. A digital bus cable connects the camera to remote electronics which provides such functions as nonuniformity correction and control of the X-ray device, while the display and operator interface is in the form of a personal computer or workstation 28. A number of suitable personal computer or workstation arrangements are commercial available and thus this portion of the illustrated system forms no part of the present invention.

The camera head shown in FIGS. 3 and 4 includes the transparent surface 22 against which the breast is compressed, allowing X-rays which have passed through the breast to excite a scintillator provided below the transparent surface, the resulting optical image being coupled to CCD board within an inner hermetically sealed housing 34.

Figure 4:
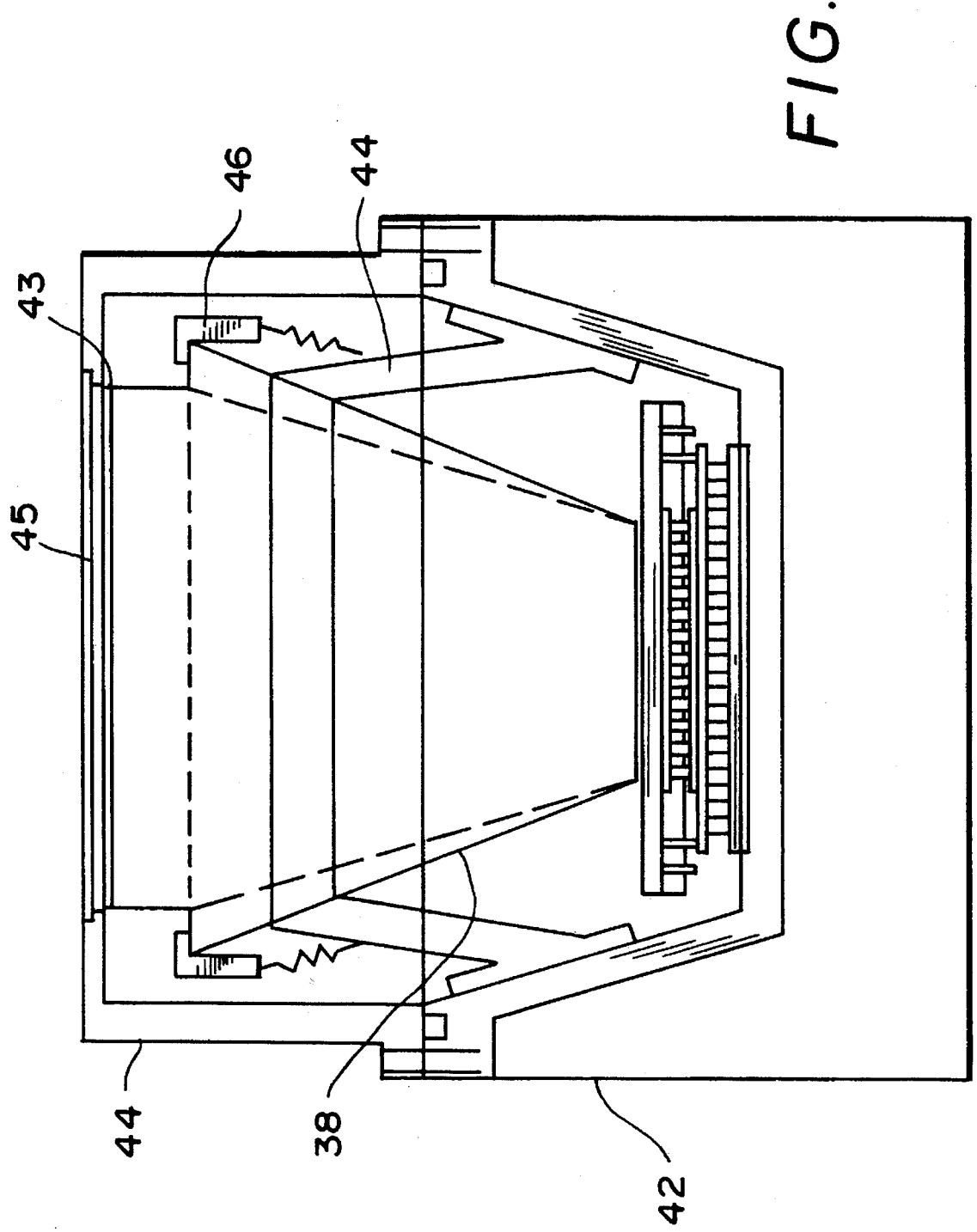
FIG. 4 is a cutaway side view of the camera head of FIG. 3.

A number of prior x-ray camera arrangements used for similar purposes are known, but the preferred device uses an especially compact and convenient arrangement, best seen in FIG. 4, in which the scintillation material is coated onto the ends of optical fibers 38 which face the glass surface 22 and the incoming X-rays and carry the image to the camera via a transparent window 45 of the inner hermetically sealed housing 34. The fiber optic coupler is made of a bundle of coherent optical fibers which are heated and stretched during manufacture to taper each fiber and thus provide appropriate magnification of the image without the need for an image intensifier or other discrete optical device. The image resulting when the phosphor coating 43 on the tips or ends adjacent the window 45 are radiated by the X-rays is thus directly coupled via fibers 38 to the CCD array 33, resulting in a high resolution image.

Heat exchange from inside the camera housing is preferably carried out by a cooling fins 40 provided in thermal contact with the camera CCD board, with a thermoelectric heat pump 35 cooling the interior of the sealed inner housing 34 to at least −25° for most efficient operation of conventional CCD arrays. While dry nitrogen may be used for cooling and desiccation purposes, the hermetic sealing of housing 34 eliminates the need for a separate desiccant, which is necessary in conventional systems because conventional rubber seals will eventually allow moisture infiltration.

The camera housing 34 is more particularly seen in FIG. 4 to include a base 42 and a cover 44 with fiber optic taper supports 44 that mount spring clips 46 for holding the fibers 38. The cover 44 mounts an X-ray transparent window 45. Included in the camera head 26 are camera head circuit boards 47, 48, and 49. These boards include, as noted above, the analog board 47, the digital board 48, and a power/control board 49 connected to the CCD board 32 by a hermetically-sealed feed-through connector (not shown).

Figure 5:
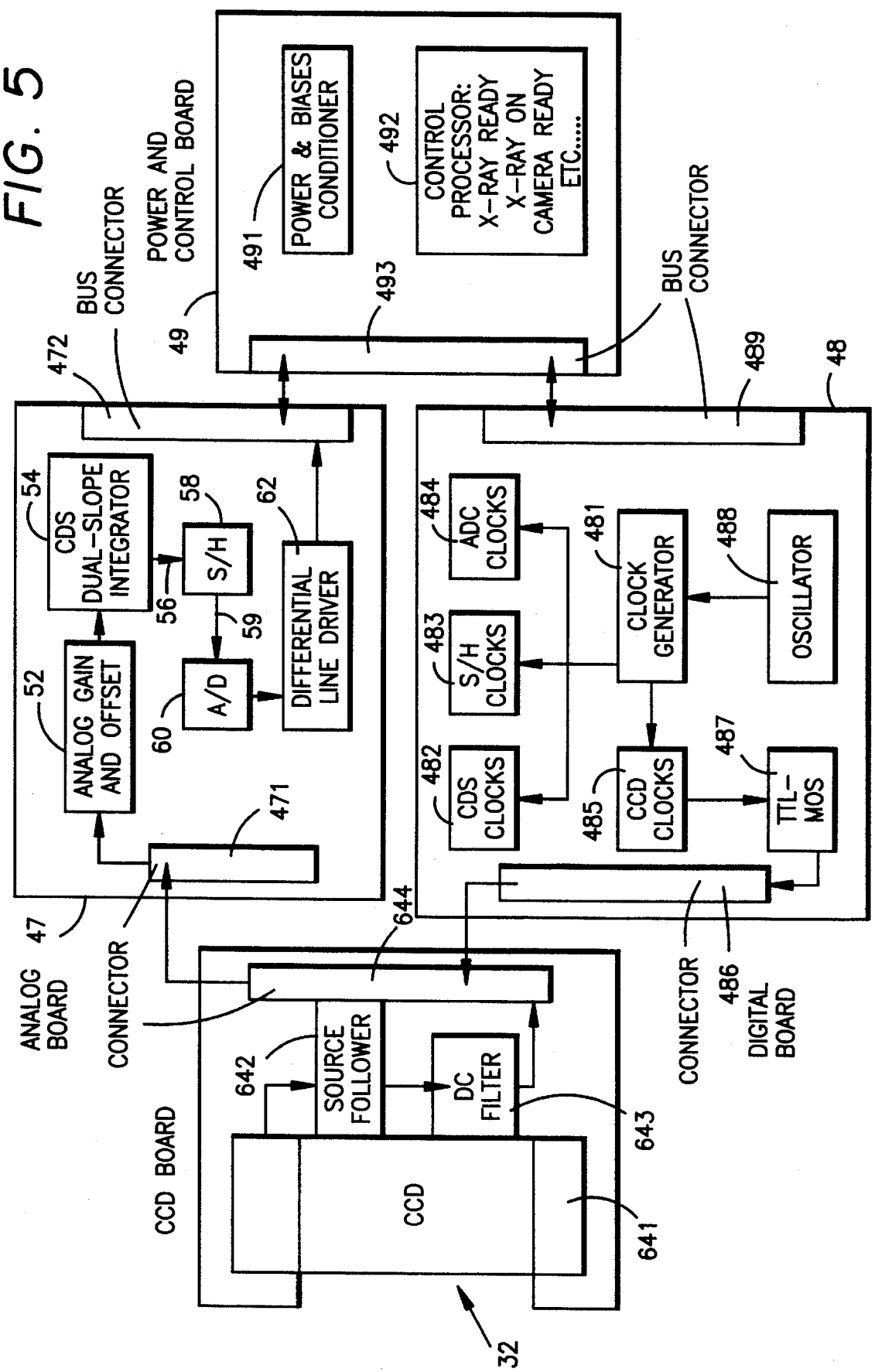
FIG. 5 is a schematic block diagram showing the camera head electronics for the camera head of FIG. 4.

An overview of the circuitry on the camera head circuit boards 47–49 is shown in FIG. 5. The analog board 47 includes an analog gain and offset amplifier 52 for feeding a correlated double sampling (CDS) circuit 54 whose output is connected to a sample and hold circuit 58. An analog-to-digital converter 60 digitizes the output of the sample and hold circuit 58 and supplies the output to a set of TTL drivers 62 for transmitting the digitized output of converter 60 over a parallel data bus, such as the RS-422 bus of the preferred embodiment, which carries the image between the analog board and the remote electronics board (described below) for further digital processing.

The digital board 48 of the camera head includes a clock signal generator 481 which supplies timing signals to respective clocks 482–485 for the CDS circuit 54, the sample and hold circuit 58, the analog-to-digital converter 59, and the CCD array 641 which is preferably in the form of an integrated circuit having appropriate clock inputs and analog outputs, the specific connections for which will depend on the specific model of integrated circuit utilized. The timing signals for the pixel array include pixel clock, line sync, and frame sync signals. The CCD clock signals are supplied to the CCD board 64 by a connector 486 via a TTL-MOS circuit 487. The digital board also includes an oscillator 488 for the clock signal generator. Power is supplied to the analog and digital boards by a power and control board 49 also situated in the camera head, and including power and bias conditioner 491 and a control processor 492 for receiving and distributing control signal from the remote signal processor. Communication between the three camera head circuit boards and the remote electronics is via bus connectors 472, 489, and 493, while the CCD board is connected respectively to the analog and digital boards by connectors 471 and 486.

Figure 6:
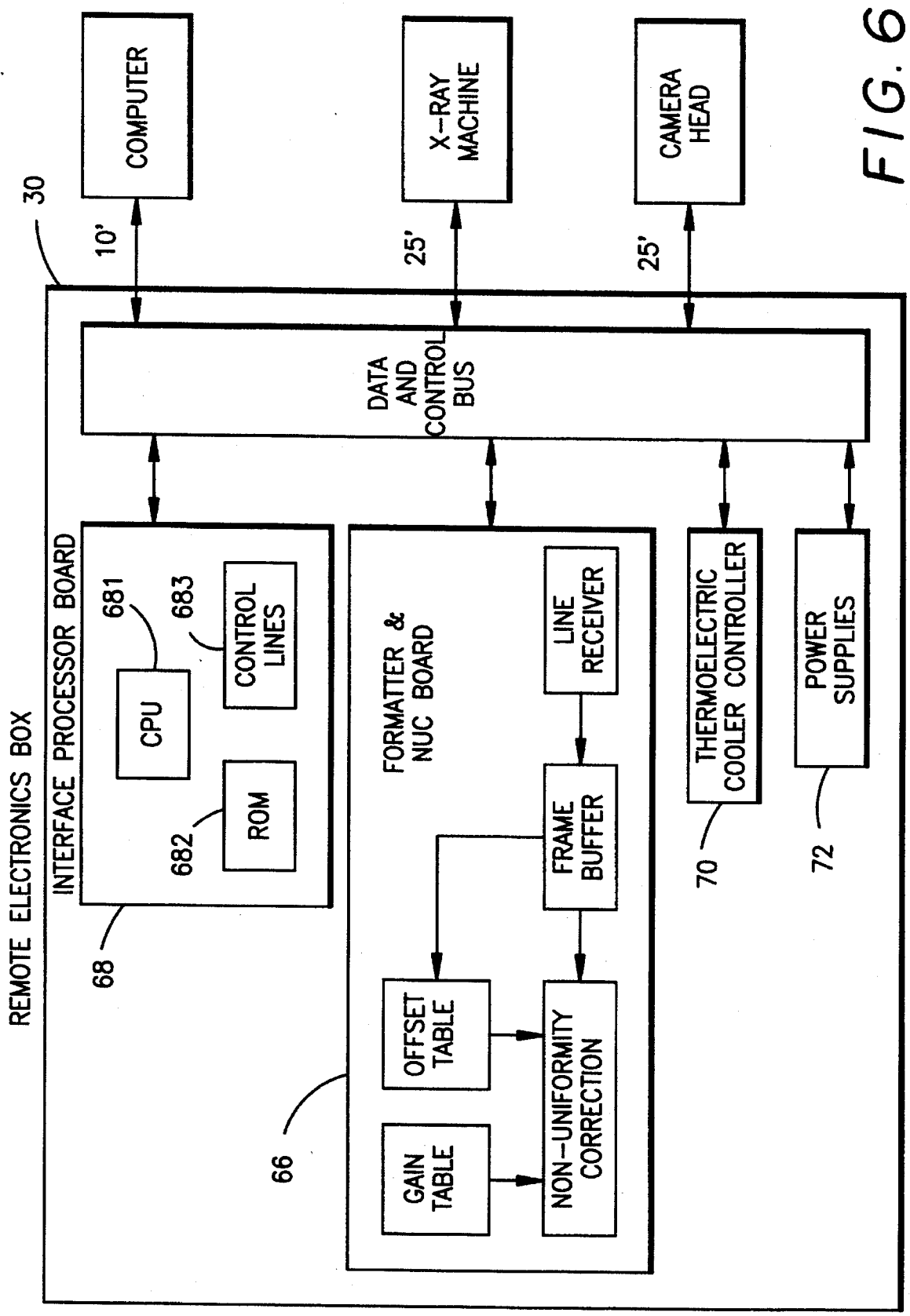
FIG. 6 is a schematic circuit diagram of the main remote digital processing circuit board for the layout shown in FIG. 5.

FIG. 6 is a block diagram illustrating a preferred circuit provided in the remote control box 30, including a formatter and non-uniformity correction board 66; an interface processor board 68; a thermoelectric cooler controller board 70 and power supplies 72. The formatter and nonuniformity board 66 receives the output from the line driver 62, i.e., the RS-422 digital data and timing signals transmitted over bus 25' from the camera head electronics boards illustrated in FIG. 6. Board 66 then re-sequences the data, generates a pixel address and stores them in a frame buffer for subsequent processing. The pixel address is used to access the offset and gain correction look-up tables from their RAM memory. At regular intervals, a black reference frame and a white reference frame are exposed. These two reference frames are used by the interface processor board to compute the gain and offset non-uniformity correction coefficients. Subsequent CCD output data are corrected for the offset and gain variations by the two correction look-up tables. This correction procedure is implemented via a hardware adder and a hardware multiplier. All correction can be set to zero under computer or manual control. Bad pixels can also be corrected in this process by flagging the address of the bad pixels and substituting with the nearest neighbors signal amplitude, gain coefficients and offset coefficients.

The interface processor board 68 contains a microcomputer 681 which controls other remote electronics box boards and provides for the remote control interface to the camera head electronics box. Other functions of the processor board include handling commands to and from the X-ray machine, interfaces to the manual pushbutton controls on the front panel, generating offset and gain correction coefficients from reference frames, computing the integration time, generating state machine codes to the camera head electronics, performing power-up built-in test and diagnostics. The processor board also contains a flash ROM memory 682 for storing look-up correction data over a power down period so that it can be used to initialize the RAM look-up tables at power-up, as well as appropriate control lines 683.

A power supply board 72 includes power supplies for the camera head and for the remote electronics. Wiring connections for the power supplies, thermal electric cooler controller, and host interface, and details of the thermal electric cooler controller and interface processor board, which preferably include opto-isolator circuitry and RS-422 drivers would be familiar to those skilled in the art and therefore are not discussed in detail herein.

The temperature controller circuitry on temperature controller board 70 is preferably in the form of closed loop temperature control circuitry. For example, a thermometer located on the cold finger in the camera head could be used to provide temperature input to a servo controller, the temperature being compared with a desired value, and the error signal used to proportionally change the current to the thermal electric cooler. The cooling rate of the CCD is preferably limited to less than 5° C. per minute in order to reduce thermal shock to the microelectronics.

Those skilled in the art will of course appreciate that implementation of the camera circuitry can take numerous forms, but that once the principles embodied in the preferred embodiment are understood, the details are a matter of routine for those skilled in the art. For example, a number of different pre-manufactured integrated circuits may used as the camera CCD array, with appropriate adjustments to the wiring and control circuits being made as required by the integrated circuit chosen. Such components as the analog gain and offset, sample and hold, A/D convertors, and so forth are well-known in the art. Also, for example, while use of field programmable gate array circuitry for generating control signals is particularly advantageous, it will be appreciated that in general such circuits are known and that, based on the above description, could easily be modified by those skilled in the art.

Having thus described the invention by reference to a specific embodiment as illustrated, those skilled in the art will appreciate that numerous variations, modifications, and substitutions of parts may be made to the preferred embodiment, and that such variations and modifications should be included in the scope thereof. Accordingly, it is to be understood that the invention is not to be limited by the above description, but rather that it is to be defined solely by the appended claims.

I claim:

1. In a precision mammographic needle biopsy apparatus, including:

an X-ray source;

a biopsy needle and an actuator for moving the biopsy needle in response to operator input;

a compression plate and a first transparent surface between which the breast is clamped during a biopsy procedure;

means including a CCD array for receiving X-rays emitted by said source which have passed through said breast, the improvement wherein:

said means for receiving X-rays comprises an X-ray camera having a housing which includes said first transparent surface, said camera housing having positioned therein:

a sealed inner housing including a second transparent surface and having situated therein said CCD array, means for converting x-rays which have passed through said second transparent surface into light and guiding said light to said CCD array, and pre-amplification means for pre-amplifying an output of the CCD array; and an analog circuit board having thereon analog processing means for receiving pre-amplified signals from said pre-amplification means within the sealed inner housing and processing the pre-amplified signals for input to an analog-to-digital converter, the analog-to-digital converter being connected to a bus connector in said camera housing;

a digital circuit board having thereon a clock signal generator for supplying timing signals to the analog processing circuitry and the analog-to-digital converter, and to the CCD array; and a power and control board having thereon means for conditioning and supplying power to the analog and digital circuit boards and means including a control processor for receiving and distributing control signals supplied by a remote signal processor, wherein said means for guiding said light to said CCD array consists of a plurality of optical fibers having ends which face the second transparent surface and ends adjacent the CCD array, said optical fibers having a scintillation material coated on the ends of the fibers which face said second transparent surface, and wherein said optical fiber are tapered such that a diameter of said fibers is less at the ends of said fibers which are adjacent the CCD array than at said coated ends.

2. Apparatus as claimed in claim 1, wherein said clock signal generator is a field programmable gate array.

3. Apparatus as claimed in claim 1, further comprising a support for supporting the CCD array and cooling fins on the support for permitting heat exchange between said inner having and said camera housing.

4. Apparatus as claimed in claim 1, further comprising means including a thermal electric cooler for reducing an operating temperature of the CCD array.

5. Apparatus as claimed in claim 1, wherein said sealed inner housing is hermetically sealed.

6. Apparatus as claimed in claim 5, wherein cooling of the interior of the sealed inner housing is provided by a servo-controlled thermoelectric heat pump.

7. Apparatus as claimed in claim 1, wherein said analog processing means includes an analog gain and offset amplifier having an input connected to the preamplification means on the CCD array, a correlated double sampling circuit having an input connected to the correlated double sampling circuit and an output connected to a sample and hold circuit, an output of the sample and hold circuit being connected to the analog-to-digital converter.

8. Apparatus as claimed in claim 1, wherein said sealed inner housing comprises a base and a cover, said cover including said second transparent surface and means including spring clips for positioning the optical fibers relative to said second transparent surface.

\* \* \* \* \*